United States Patent [19]

Inoue et al.

[11] Patent Number: 5,762,944
[45] Date of Patent: Jun. 9, 1998

[54] ANTITHROMBOTIC RESIN, ANTITHROMBOTIC TUBE, ANTITHROMBOTIC FILM AND ANTITHROMBOTIC COAT

[75] Inventors: Fujio Inoue; Masamitsu Izumi, both of Naruto; Satoru Hayashi, Itano-gun; Nobuhisa Tsutsumi; Kunihiro Fukuoka, both of Tokushima, all of Japan

[73] Assignees: Otsuka Pharmaceutical Factory, Inc., Tokushima; Nisshinbo Industries, Inc.; Otsuka Pharmaceutical Co., Ltd., both of Tokyo, all of Japan

[21] Appl. No.: 376,431

[22] Filed: Jan. 23, 1995

Related U.S. Application Data

[63] Continuation of Ser. No. 039,164, Apr. 12, 1993, abandoned.

[30] Foreign Application Priority Data

| May 29, 1992 | [JP] | Japan | 4-139389 |
| Oct. 1, 1994 | [JP] | Japan | 3-253942 |

[51] Int. Cl.$^6$ .................... A61L 33/00
[52] U.S. Cl. .......... 424/400; 424/423; 424/486; 604/266; 523/112; 514/822
[58] Field of Search .................... 424/400, 423; 523/112; 514/822; 604/266

[56] References Cited

U.S. PATENT DOCUMENTS

| 4,353,996 | 10/1982 | Marconi et al. | 523/105 |
| 4,371,686 | 2/1983 | Yamamoto | 528/76 |
| 4,537,894 | 8/1985 | Blanchard et al. | 514/301 |
| 4,600,652 | 7/1986 | Solomon et al. | 424/423 |
| 4,678,660 | 7/1987 | McGary et al. | 424/423 |
| 4,822,615 | 4/1989 | Iwata et al. | 424/423 |
| 5,061,254 | 10/1991 | Karakelle et al. | 604/265 |
| 5,132,208 | 7/1992 | Narayanan et al. | 424/423 |
| 5,153,003 | 10/1992 | Kurihara et al. | 424/423 |
| 5,167,960 | 12/1992 | Ito et al. | 424/423 |

FOREIGN PATENT DOCUMENTS

| 0335308 | 10/1989 | European Pat. Off. |
| 0404517 | 12/1990 | European Pat. Off. |
| 3239318 | 5/1983 | Germany |
| 3341847 | 6/1985 | Germany |
| 50-139173 | 4/1974 | Japan |
| 53-117281 | 10/1978 | Japan |
| 54-135493 | 10/1979 | Japan |
| 58-92363 | 6/1983 | Japan |
| 61-168365 | 7/1986 | Japan |
| 61-204219 | 9/1986 | Japan |
| 64-15058 | 1/1989 | Japan |

OTHER PUBLICATIONS

Japanese Patent Publication No. 1–38504 dated 1989 and Abstract.

Biomaterials, vol. 8, No. 6, Nov. 1987, Giuldford, Surrey, GB: pp. 464–472; Ito et al "Attachment and Proliferation of Fibroblast Cells on Polyetheruretane Urea Derivatives"; p. 464, col. 2, line 14–p. 465, col. 1, line 23.

*Primary Examiner*—Amy Hulina
*Attorney, Agent, or Firm*—Sughrue,Mion,Zinn,Macpeak & Seas, PLLC

[57] ABSTRACT

The invention presents an antithrombotic resin which is prepared by blending at least one type of antithrombotics, in polyurethane or polyurethane urea polymerized by using at least one type of polyether diol selected from the group consisting of polyol containing a polyoxyethylene group expressed in formula (I)

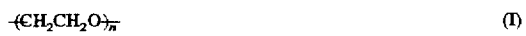

$$-(CH_2CH_2O)_n-\qquad(I)$$

(where n is a number-average degree of polymerization of 1 to 100) and polyol containing a polyoxyethylene group expressed in formula (II)

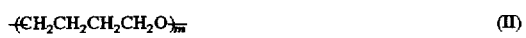

$$-(CH_2CH_2CH_2CH_2O)_m-\qquad(II)$$

(where m is a number-average degree of polymerization of 1 to 100). This antithrombotic resin is capable of eluting the antithrombotic in the blood for a long time at high concentration. By using the antithrombotic resin of the invention, antithrombotic tube, antithrombotic film, antithrombotic coat, and others are obtained.

11 Claims, 8 Drawing Sheets

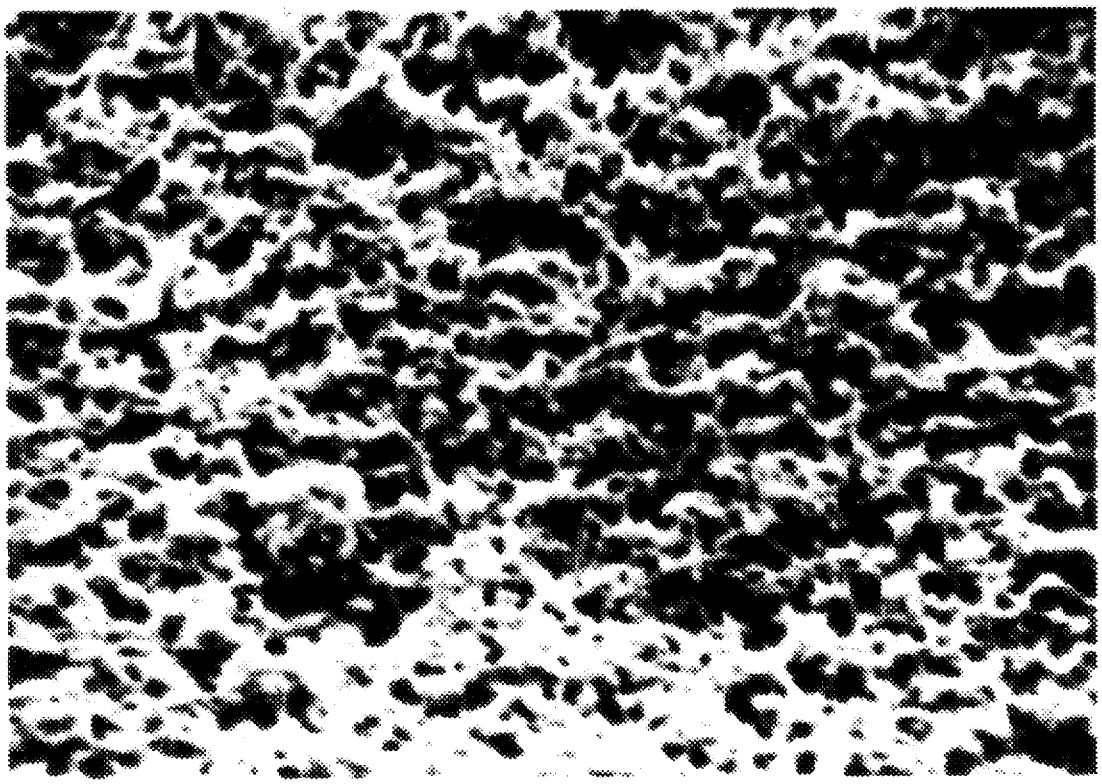
FIG. IA
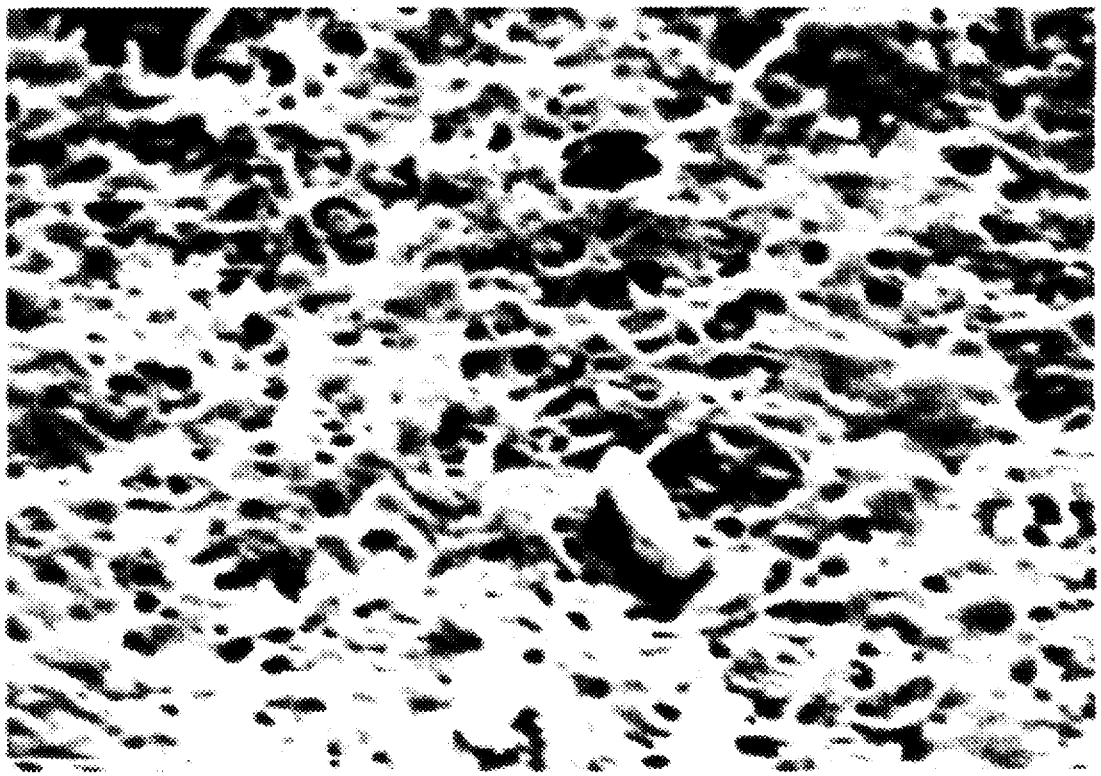
FIG. IB

ANTITHROMBOTIC RESIN, ANTITHROMBOTIC TUBE, ANTITHROMBOTIC FILM AND ANTITHROMBOTIC COAT

This is a Continuation of application Ser. No. 08/039,164 filed Apr. 12, 1993 now abandoned.

TECHNICAL FIELD

The present invention relates to an antithrombotic resin, antithrombotic tube, an antithrombotic film, and antithrombotic coating used in artificial blood vessels and the like.

BACKGROUND ART

Generally, medical materials which contact directly with the blood, such as artificial organs, artificial blood vessels and blood transfusion apparatus, are required to possess biological affinity such as blood compatibility and biocompatibility, and mechanical properties such as flexibility, elasticity, durability, and wet toughness, as well as a high antithrombotic property. As such materials, hitherto, medical materials heightened in antithrombotic property by adding heparin or other antithrombotic agent to polymer materials have been known. It is, however, difficult to elute the antithrombotic agent for a long period at a high concentration. It is also difficult to couple heparin and medical materials directly, and hence a cationic polymer is used as a binder for medical materials and heparin. The antithrombotic property of heparin is expressed when heparin is released from the medical material and is coupled with antithrombin III in blood, but the cationic polymer is exposed in the release marks of heparin. The cationic polymer possesses an action for agglutinating negatively charged platelets, and works in a direction for producing platelet thrombi, which is inconvenient.

Besides, after transplantation of blood vessel, there is a method of orally administering antithrombotics periodically. In this method, the formation of thrombi may be reduced, but since the pharmacological action spreads over the whole body, adverse side effects may be caused, therapeutic effects may be poor, and other problems are pointed out.

On the other hand, materials excellent in blood compatibility without using antithrombotics are also developed. In the field of artificial blood vessels, for example, Dveysky's artificial blood vessel having Dacron fiber texture manufactured by USOI of the United States, and an artificial blood vessel having drawn structure made of polyethylene tetrafluoride manufactured by Gore of the United States are known. Still more, various artificial blood vessels using polyurethane or polyurethane urea of high antithrombotic property are being studied. Ultimately, however, all of them involve functional problems such as thrombotic occlusion due to hypertrophy of false intima, and therefore, at present, relatively safe transplantations are limited to arteries larger than 5 mm in diameter, and they cannot be applied to fine arteries of less than 4 mm in diameter or veins with small blood flow.

Presently, however, there is a keen demand for the development of artificial blood vessels having a small aperture in the field of medical care. Applications of artificial blood vessels of having a small aperture include, among others, the following. In the treatment of myocardial infarction, when transplanting a blood vessel to the myocardial surface, an artificial blood vessel is temporarily transplanted in the heart to be used as a substitute until a blood vessel suitable for transplantation is obtained, and the artificial blood vessel transplanted as a substitute at this time is desired to be 4 mm or less in aperture. Or, when grafting a skin piece, for example, when grafting a femoral skin piece to the chest, if the femoral skin is cut off and is immediately transplanted in the desired area of the chest, since the skin graft is cut off from all blood vessels, the possibility of necrosis of the skin is high, which is not desirable. As a method of solving this problem, the skin graft and the transplanting area are connected with artificial blood vessels to allow the blood to flow into the skin graft so that the risk of necrosis of the skin may be avoided. Since the blood vessels in the skin are fine, artificial blood vessels of small aperture are needed.

It is hence a primary object of the invention to present an antithrombotic resin capable of solving the above technical problems, and eluting the antithrombotics in the blood for a long period at a high concentration.

It is another object of the invention to present an antithrombotic tube, preferably used in artificial blood vessels having a small aperture or the like, that does not cause thrombotic occlusion even if the aperture is 4 mm or less.

It is another object of the invention to present an antithrombotic film preferably usable as the film for use in cataplasm or the like for applying on the affected surface of burns or the like or other medical film.

It is a further object of the invention to present an antithrombotic coating capable of providing the surface of medical apparatus with antithrombotic property.

DISCLOSURE OF THE INVENTION

An antithrombotic resin of the invention is prepared by blending at least one type of antithrombotic agent, in polyurethane or polyurethane urea polymerized by using at least one type of polyether diol selected from the group consisting of polyol containing a polyoxyethylene group expressed in formula (I)

     (I)

where n is a number-average degree of polymerization of 1 to 100 and polyol containing a polyoxytetramethylene group expressed in formula (II)

     (II)

where m is a number-average degree of polymerization of 1 to 100.

The antithrombotic tube of the invention is manufactured by forming the antithrombotic resin of the invention in a tube form, which is preferably used, for example, as an artificial blood vessel.

The antithrombotic film of the invention is manufactured by forming the antithrombotic resin of the invention in a film form, and when it is used as a medical film such as cataplasm poulticed to cure burns or the like, since the film can be prepared so that the film itself possesses the moisture absorbing and swelling property, the film absorbs the exudate from the wound, so that pooling of exudate may be prevented as required in burn covering film. Prevention of bacterial infection is another required property, and since the film of the invention does not allow bacteria to permeate, it has sufficient merit in this respect. The film conventionally used to cover burns had multiple pores made in a silicone film in order to prevent deposit of plasma protein or formation of hematoma. On the other hand, the film of the invention possesses both a performance of the release of antithrombotics and a moisture absorbing and swelling property, and is therefore capable of treating more directly and effectively, as compared with the conventional perforated film.

The antithrombotic coating of the invention is manufactured by coating the surface of medical apparatus with the antithrombotic resin of the invention. Applicable medical apparatuses may include, for example, expandable metallic stents inserted in the blood vessel for expanding the blood vessel (specifically known in the tradenames of Gianturco Z Stent, Modified Gianturco Z Stent, Palmax Stent, Wallstent and Strecker Stent). When the surface of such medical apparatuses is coated with the antithrombotic resin of the invention to be provided with antithrombotic property, it is effective to prevent inapplicability in indwelling or use of the apparatuses due to freshly formed thrombi when these medical apparatuses come to contact with blood, and also to prevent early formation of thrombi, thereby bringing about the advantages of suppressing the hypertrophy of the intima of blood vessel and executing the initial therapeutic purposes of the apparatuses.

Of the invention, in particular, the antithrombotic tube is manufactured in the procedure comprising a step for mixing antithrombotics in a solution of polyurethane or polyurethane urea polymerized by using at least one type of polyether diol selected from the group consisting of a polyol containing a polyoxyethylene group expressed in formula (I) and a polyol containing a polyoxytetramethylene group expressed in formula (II), a step for applying the obtained polymer solution containing antithrombotics on the surface of a core rod, a step for forming a tube by immersing the core rod coated with the polymer solution in a solidifying solution and solidifying the polymer on the surface of the core rod, and a step for drawing out the formed tube from the core rod and drying.

As the polyether diol used as the material for polyurethane or polyurethane urea, the following examples are preferably used. (1) A polyol containing a polyoxyethylene group expressed in formula (I)

  (I)

where n is same as defined above; and (2) A polyol containing a polyoxytetramethylene group expressed in formula (II)

  (II)

where m is same as defined above.

Examples of polyol include the following.

(i) A polyol composed of only polyoxyethylene group or polyoxytetramethylene group, that is, polyoxyethyelene glycol or polyoxytetramethylene glycol;

(ii) A polyol containing a polyoxyethylene group in part, for example, a polyol having polyoxyethylene group and polyoxytetramethylene group, a polyol having polyoxyethylene group and polyoxypropylene group expressed in formula (III):

  (III)

(where l is a number-average degree of polymerization of 1 100), a polyol having ethylene oxide added to both ends of polydimethyl siloxane, a polyol having ethylene oxide added to both ends of diol wherein the methyl group of bisphenyl A is re-placed by trifluoromethyl group, and a polyol having ethylene oxide added to both ends of bisphenol S; and (iii) A polyol containing a polyoxytetramethylene group in part, for example, a polyol having a polyoxyethylene group and a polyoxytetramethylene group, which is mentioned in (ii), a polyol having a polyoxypropylene group and a polyoxytetramethylene group, and a copolymer of tetrahydrofran and ε-caprolactone.

In the invention, in the case of (ii) or in the case of using a mixture of two or more types of polyurethane or polyurethane urea, the rate of elution of antithrombotics may be adjusted, while the mechanical strength and swelling property of the resin can also be adjusted. Among them, the swelling property can be adjusted by selecting the type if there is only one type of polyol or one type of polyurethane or polyurethane urea.

As the polyurethane or polyurethane urea used in the invention, the polyether type is preferable to the polyester type in that the resistance is high in hydrolysis in a living body.

The polyether diol such as polyoxyethylene glycol used in the invention is in a range of molecular weight of 400 to 3500, preferably 500 to 2500. When using the polyether diol of which molecular weight exceeds 3500, the mechanical strength is weak as polyurethane artificial blood vessel, or when using the polyether diol of which molecular weight is less than 400, the polyurethane artificial blood vessel lacks flexibility, and neither case is preferable.

These polyether diols are caused to react by polyaddition with organic diisocyanate of mol excess. The molar ratio of organic diisocyanate to polyether diol is about 1.2 to 12, and when low molecular multifunctional substance forming a urea bond when reacting with isocyanate group is used as a chain extender, the range is preferably 1.2 to 2.5. The reaction may be done in ordinary method in the presence or absence of solvent, so that a prepolymer possessing a diisocyanate group at the end is obtained.

The preferable examples of diisocyanate in the invention include, among others, 2,4-tolylene diisocyanate, 2,6-tolylene diisocyanate, p-phenylene diisocyanate, 4,4'-diphenylmethane diisocyanate, 3,3'-dimethyl-4,4'-diphenylmethane diisocyanate, 4,4'-biphenylene diisocyanate, 1,5-naphthylene diisocyanate, tetramethylene diisocyanate, hexamethylene diisocyanate, p-xylene diisocyanate, m-xylene diisocyanate, methylene-bis-4,4'-cyclohexyl diisocyanate, 4,4'-dicylohexylmethane diisocyanate, isophorone diisocyanate, lysine diisocyanate, fluorine-contained diisocyanate, and other known aromatic, aliphatic and alicyclic diisocyanates. These organic diisocyanates may be used either alone or in combination of two or more types.

Practical examples of the solvent are, among others, N,N,-dimethyl formamide, N,N-dimethylacetamide, N-methyl pyrrolidone, N,N'-tetramethyl urea, hexamethyl phosphoramide, tetramethylne sulfone, dimethyl sulfoxide, tetrahydrofuran, and other polar solvents.

Thus obtained isocyanate modified intermediate polymer (prepolymer) is caused to react with a chain extender to manufacture polyurethane or polyurethane urea of high molecular weight. This reaction is conducted in lump or in solution. Here, when using a chain extender which forms a urea bond when reacting with the isocyanate group, the reaction is done in such a solvent as mentioned above, and it is particularly desired to use dry solvents such as N,N-dimethyl formamide, N,N-dimethylacetamide and dimethyl sulfoxide.

The chain extenders used in the invention may be roughly classified into such low molecular multifunctional substances that form a urea bond when reacting with an isocyanate group, such as hydrazine, aliphatic diamine, aromatic diamine, alicyclic diamine, heterocyclic diamine, carbohydrazide, hydrazide dicarboxylate and water (hereinafter called group I), and such low molecular multifunctional substances that form a urethane bond when reacting with an isocyanate group, such as aliphatic diol, aromatic diol, and alicyclic diol (hereinafter called as group II). Practical compounds belonging to group I include, for example, hydrazine, ethylene diamine, propylene diamine, butylene diamine, trimethylene diamine, pentamethylene diamine, 1,4-diaminocyclohexane, 1,3-diaminocyclohexane, m-phenylene diamine, p-phenylene diamine, m-xylene diamine, p-xylene diamine, methylimino bispropylamine, 4,4'-diaminodiphenyl methane, pyerazine, N,N'-dialkylethylene diamine, carbodihydrazide, hydrazide oxalate, dihydrazide adipate, and water. Practical compounds belonging to group II include, for example, ethylene glycol, propylene glycol, diethlene glycol, 1,4-butane diol, 1,6-hexane diol, 1,10-decamethylene diol, 2,5-dimethyl-2,5-hexane diol, neopentyl glycol, 1,4-cyclohexane dimethanol, bis(β-hydroxyethoxy)benzene, p-xylene diol, dihydroxy ethyltetrahydrophthalate, trimethylolpropane, glycerin, 2-methylpropane-1,2,3-triol, pentaerythrite, ethanolamine, and methylethanolamine. These compounds may be used either alone or in combinations of two or more types. In these compounds, monofunctional compounds, for example, primary amines such as ethylamine, butylamine, and porpylamine, secondary amines such as diethylamine, di-n-butylamine, and dipropylamine, and monoalcohols such as methanol, ethanol, propanol, and butanol may be contained by a slight portion as an adjuster of degree of polymerization. When group I is used as the chain extender, the quantitative rate of prepolymer and chain extender may be equivalent stoichiometrically, or the chain extender may be slightly more, but when group II is used as the chain extender, the prepolymer may be greater than the chain extender stoichiometrically.

The degree of swelling by water and moisture absorption rate of polyurethane or polyurethane urea can be mainly adjusted by the type and molecular weight of polyether diol, and the content of polyether diol in the polymer. For example, when a copolymer of ethylene oxide and propylene oxide of the same molecular weight is used as a polyether diol, as the content of a polyethylene group contained in polyether diol becomes higher, the degree of swelling or moisture absorption rate tends to increase as known empirically. Or when a polyoxyethylene glycol of the same molecular weight is used as polyether diol, as the content of the polyoxyethylene group contained in the polymer becomes smaller, the degree of swelling or moisture absorption rate declines.

Here, the "degree of swelling by water" refers to the change in the thickness or length when a resin test piece is immersed in water for a specific period, and the "moisture absorption rate" denotes the weight change when a resin test piece is immersed in water for a specific period. These values were obtained in conformity with JIS K 7114 (Testing Method for Evaluation of the Resistance of Plastics of Chemical Substances), except that 0.5 mm thick disc test pieces were put in a humidistat maintained at 37° C.±1° C. for 7 days. That is, the test piece was completely immersed in water at 37° C.±1° C. put in a container, the container was sealed, and put in a humidistat maintained at 37° C.±1° C. for 7 days, and the length or thickness was measured before and after immersion in winter, so that the degree of swelling could be calculated from equation (1). By measuring the weight before and after immersion, the moisture absorption rate can be determined from equation (2).

$$\text{Degree of swelling (\%)} = \frac{L_2 - L_1}{L_1} \times 100 \quad (1)$$

where
$L_1$: length or thickness of test piece before test (mm)
$L_2$: length or thickness of test piece after test (mm)

$$\text{Moisture absorption rate (\%)} = \frac{W_2 - W_1}{W_1} \times 100 \quad (2)$$

where
W1: weight of test piece before test (g)
W2: weight of test piece after test (g)

The antithrombotics agents capable of being blended in a resin are cilostazol, ticlopidine hydrochloride, and limaprost α-cyclodextrin clathrate, and in particular it is desired to use cilostazol. The content of the antithrombotic is desired to be in a range of 0.1 to 50% by weight to the polyurethane or polyurethane urea. If the content of the antithrombotic is less than 0.1% by weight, although the sustained-release effect of antithrombotic into the blood is noted, the thrombus preventive effect is low, and the effect of addition is not expected substantially. On the other hand, if the content exceeds 50% by weight, the forming property is poor, and if formed scarcely, the formed matter is significantly lowered in the mechanical or dynamic properties, and it is not practical.

Next, a manufacturing method of the antithrombotic tube of the invention is explained. A specified quantity of antithrombotic is charged directly or in solution form in a solution of one type or two or more types of polyurethane or polyurethane urea, and blended violently to dissolve or disperse. In succession, this liquid is uniformly applied on the outer circumference of a columnar core rod, and is led into a solidifying bath to solidify (form) the resin on the core rod. After forming, by sufficiently cleaning in organic solvent or water, the tube is drawn out of the core rod, and cleaning is further repeated, and it is dried.

Before mixing or dispersing the antithrombotic, by preliminarily sedimenting the polymer by using bad solvent such as methanol, ethanol, acetone, benzene, acetonitrile, water or other dilute solvent, and sufficiently cleaning by Soxhlet extration or other method, the solvent, unreacted portion or impurity in the polymer may be removed. As the solvent for dissolving the antithrombotic, any known organic solvent or water may be used, but the same organic solvent as the polymer solution is desired. As the core rod, any core rod made of stainless steel, glass, fluoroplastics, polyethylene, polypropylene or the like may be used. As the method of applying polymer solution on the core rod, dipping, flowing or other known method may be employed.

As the solidifying liquid, bad solvent of polymer, for example, water, methanol, ethanol, propanol butanol or other alcohols, and ketones represented by acetone may be used either alone or in mixture of two or more types, and if necessary a mixture of strong solvent of polymer, such as N,N-dimethylformamide, N,N-dimethylacetamide, dimethylsulfoxide, tetrahydrofuran may be contained by up to 50% to the bad solvent. However, the solubility of the antithrombotic must be taken into consideration. That is, elution of antithrombotic into the solidifying liquid during solidification of the polymer should be avoided as far as possible. Therefore, if the solubility of the antithrombotic of the polymer in dilute solvent is strong, a solvent for reducing the solubility of the antithrombotic is mixed in the dilute solvent of polymer as the solidifying liquid, and the polymer and the antithrombotic contained therein are solidified simultaneously.

As other method of forming the antithrombotic tube, any known fusion technique may be employed, but generally it is difficult to form polyurethane urea by fusion method, and it is also hard to form into a tube by the fusion method when using an antithrombotic material that is low in heat resistance. In contrast, by the solution forming method mentioned above, it is suitable to the tube forming by using a material hard to form by the fusion method. Anyway, the materials that can be formed by the fusion method may be formed either by the solution forming method or fusion method without any particular limitations.

The antithrombotic tube of the invention is a non porous tube and a porous tube having multiple pores in a diameter of about 1 to 3 µm favorable for forming the intima of the blood vessel. Among them, the porous tube is generally about 1 to 10 mm in inside diameter and about 5 to 2,000 um in wall thickness in a dry state, and especially for use as artificial blood vessel, it is desired to have the inside diameter of about 1 to 6 mm and the wall thickness of about 100 to 400 µm.

The antithrombotic film of the invention is manufactured by forming into a film by various known film forming methods, such as the method of coating a mold releasing paper with solution and drying and removing, the method of coating the woven, knit or nonwoven cloth directly with solution, or impregnating, and drying and removing solvent, and the method of solution flowing process. The film should be usually about 5 to 2,000 µm in thickness, or preferably 30 to 300 µm, for use as medical material such as cataplasm.

The antithrombotic coat of the invention is manufactured by immersing the medical apparatus into a polymer solution containing antithrombotics, for example, the same that is used in the antithrombotic tube, immersing this medical apparatus in a solidifying liquid to solidify the polymer on the surface of the medical apparatus, thereby forming a coat. The thickness of the coat is usually 5 to 1,000 µm, or preferably 5 to 100 µm.

INDUSTRIAL APPLICABILITY

Figure 1C:
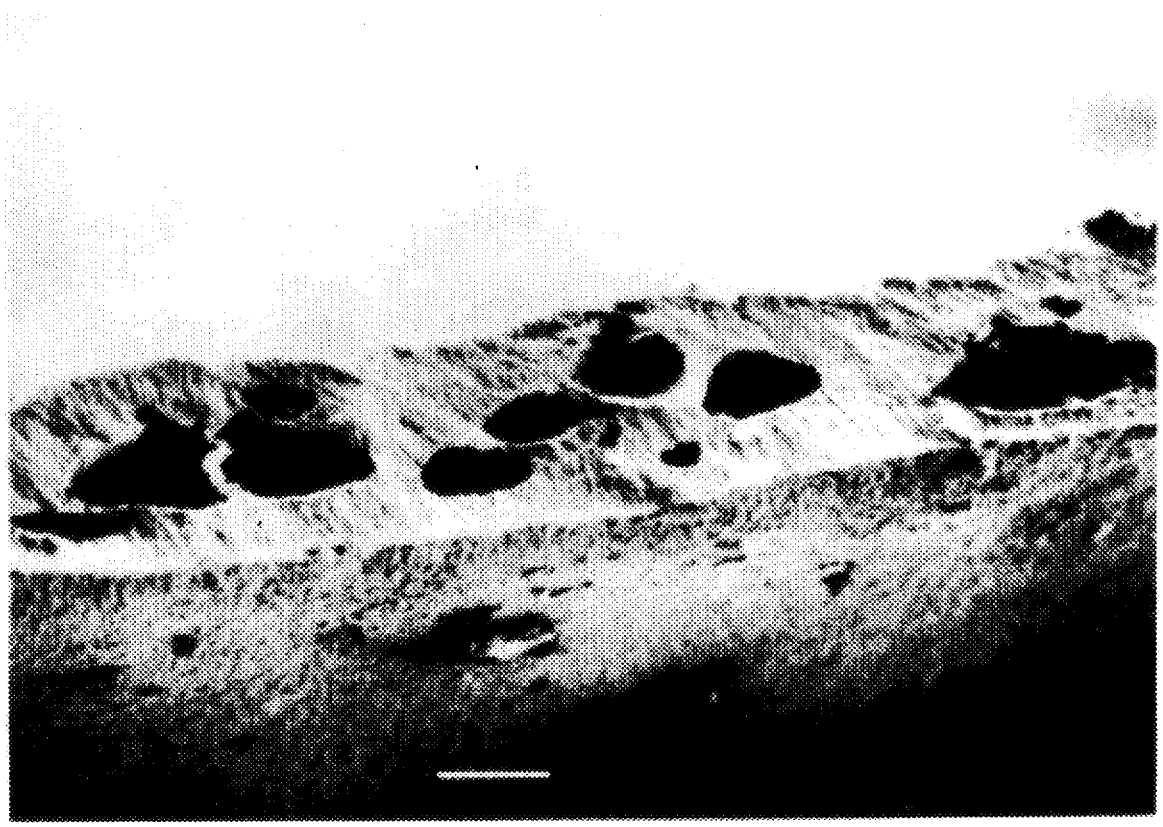
FIGS. 1 (a) to (d) are electron microscopic photographs showing that the tube obtained in Example 6 is porous, FIG. 1 (a) is a microscopic photograph (3,000 times) showing the outer surface of the tube, FIG. 1 (b) is a microscopic photograph (3,000 times) showing the inner surface of the tube, FIG. 1 (c) is a microscopic photograph (100 times) showing the section obtained by slicing the tube along the axial direction thereof, and FIG. 1 (d) is a microscopic photograph (3,000 times) showing the inside of hole existing in the section of the FIG. 1 (c)

The antithrombotic resin of the invention is capable of eluting the antithrombotic into the blood for a long period at high concentration. The antithrombotic tube of the invention made of such antithrombotic resin does not allow thrombi to form if used in a small aperture of 4 mm or less, so that it may be preferably used in artificial blood vessel or the like.

The antithrombotic film of the invention obtained by using such an antithrombotic resin is preferably the medical film, such as cataplasm, used in curing burns or the like.

The antithrombotic coat of the invention obtained by coating the surface of a medical apparatus with the antithrombotic resin provides the medical apparatus with the antithrombotic property, and hence it is possible to prevent inapplicability of the apparatus in indwelling or use due to freshly formed thrombi when the medical apparatus contacts with the blood, to suppress hypertrophy of the intima of the blood vessel by preventing early formation of thrombi, and to achieve the initial therapeutic purpose of the apparatus.

EXAMPLES

The invention is further described below while referring to some of the embodiments and test examples, but it must be noted that the invention is not limited to these examples alone.

Example 1

350 parts (parts by weight, same hereinafter) of polyoxyethylene glycol with a molecular weight of 2000, and 87.5 parts of 4,4'-diphenyl methane diisocyanate were allowed to react with each other for 1 hour at 130° C. in a dry nitrogen atmosphere, and a prepolymer having an isocyanate group at the end was obtained. To this prepolymer, 834 parts of dry N,N-dimethylacetamide (DMAC) was added and dissolved, and stirred for about 2 hours at room temperature. Consequently, while violently stirring the obtained solution, a chain extender solution dissolving well 10.5 parts of ethylene diamine in 1380 parts of dry DMAC was gradually added. The solution was heated to 50° C., and stirred for about 5 hours, and a viscous stock solution with a viscosity of 300 poise was obtained.

When a large quantity of methanol was gradually added while stirring the stock solution, the solution became milky white, and a sediment of polymer was obtained. The sediment was filtered, and washed in an abundant volume of water, and dried sufficiently. By sufficient Soxhlet extraction in the sequence of acetone, ethanol and water, polyurethane urea was obtained. The degree of swelling by water and moisture absorption rate of this material were investigated by the method conforming to JIS K 7114, and the degree of swelling was found to be 26% and the moisture absorption rate was 120%.

To 18 parts of the obtained sediment of polyurethane urea, 42 parts of DMAC was added and dissolved well, which was obtained as a polymer mother liquor. As antithrombotic, 1.8 parts of cilostazol was added to 16.2 parts of DMAC and dissolved sufficiently, and this mixture was added to the polymer mother liquor, and blended violently. The obtained liquid was uniformly applied on the surface of a stainless steel bar of 3.0 mm in outside diameter, and immersed in 50° C. water bath for 10 minutes to be solidified. The obtained tube was drawn out the stainless steel bar, washed with a large amount of water, and dried for 48 hours at 50° C., 1 mmHg to remove DMAC and water.

The obtained tube was, in dry state, 2.3 mm in inside diameter and 0.6 mm in wall thickness, which was favorable as artificial blood vessel. When it was put in a physiological saline at pH 7.4, it began to swell immediately, reaching the degree of swelling of 25% in about 10 minutes, and achieved the state of equilibrium.

Example 2

A sediment of polyurethane urea was obtained in the same manner as in Example 1, except that 4,4'-dicyclohexylmethane diisocyanate was used, instead of 4,4'-diphenylmethane diisocyanate as diisocyanate. Its degree of swelling in water and moisture absorption rate were determined in the same method as in Example 1, and the degree of swelling was 30% and the moisture absorption rate was 130%. Furthermore, a DMAC solution adding cilostazol to this polymer at a rate of 10:1 was uniformly applied on the surface of a stainless steel bar of 3.0 mm in outside diameter, and immersed in 40° C. water bath for 10 minutes to be solidified. The obtained tube was drawn out of the stainless steel bar, and washed with a large quantity of water, and dried for 48 hours at 50° C., 1 mmHg to remove the DMAC and water. The obtained tube was, in dry state, 2.6 mm in inside diameter and 0.8 mm in wall thickness, which was an antithrombotic tube usable as an artificial blood vessel.

Example 3

To vary the degree of swelling and moisture absorption rate of the tube in Example 1, the polyol was changed. Specifically, as polyether diol, a block copolymer having ethylene oxide added to both ends of polyoxytetramethylene glycol and having molecular weight of 2000 and the content of ethylene glycol of about 29 mol %. The other preparation conditions were the same as in Example 1, and polyurethane urea with degree of swelling of 5% and moisture absorption rate of 7% was obtained. To 20 parts of this polymer, 60 parts of DMAC was added and dissolved well, which was used as a polymer mother liquor. To 28.0 parts of DMAC, 2.0 parts of cilostazol was added as the antithrombotic and dissolved sufficiently, and this mixture was added to the polymer mother liquor, and mixed violently. The obtained liquid was uniformly applied to the surface of a stainless steel bar of 4.0 mm in outside diameter, and immersed in 40° C. water bath for 20 minutes to be solidified. The obtained tube was drawn out of the stainless steel bar, and washed in a sufficient amount of water, and dried in air overnight, and dried in vacua for 60 hours at 30° C., 0.1 mmHg to remove the residual DMAC and water by force. The obtained tube was, in dry state, 3.0 mm in inside diameter and 0.4 mm in wall thickness, and was appropriate as an artificial blood vessel. When it was put in a physiological saline at pH 7.4, it began to swell immediately, reaching the degree of swelling of 5% in about 10 minutes, and achieved the state of equilibrium.

Example 4

63.3 parts of polyoxyethylene glycol with a molecular weight of 2000, and 29.5 parts of 4,4'-diphenylmethane diisocyanate were caused to react for 2 hours at 120° C. in a dry nitrogen atmosphere, and a prepolymer possessing an isocyanate group at the end was obtained. This prepolymer was moderately stirred and cooled to 70° C. Successively, while agitating violently, 11.6 parts of 1,4-butanediol was gradually added. In about 5 minutes after addition, the reaction product was taken out of the synthesis tank, and put in a thermostatic oven controlled at 40° C. and relative humidity of 80% for 24 hours. Then the finely pulverized reaction product was dried sufficiently, and charged into a extruder, and pellets were obtained from the extruder nozzle at the set temperature of 220° C. The obtained pellets were thermoplastic polyurethane that can be formed by extrusion, and the nitrogen content of the polymer was 3.3%. When the degree of swelling in water and moisture absorption rate of the polyurethane pellets were measured in the method conforming to JIS K 7114, and the degree of swelling was 30% and the moisture absorption rate was 90%.

To 15 parts of the obtained pellet-form polyurethane, 38.5 parts of DMAC was added and dissolved well, which was used as a polymer mother liquor. Next, as an antithrombotic, 1.5 parts of cilostazol was added to 15 parts of DMAC and dissolved sufficiently, and this mixture was added to the polymer mother liquor, and mixed violently. The obtained liquid was uniformly applied on the surface of a stainless steel bar of 3.0 mm in outside diameter, and immersed in 40° C. water bath for 10 minutes to be solidified. The obtained tube was drawn out of the stainless steel bar, washed in a sufficient amount of water, and dried for 48 hours at 40° C., 0.1 mmHg to remove the DMAC and water.

The obtained tube was, in dry state, 2.9 mm in inside diameter and 0.8 mm in thickness, and was suitable as an artificial blood vessel. When it was put in a physiological saline at pH 7.4, it began to swell immediately, reaching the degree of swelling of 28% in about 10 minutes, and achieved the state of equilibrium.

Example 5

500 parts of polyoxyethylene glycol with a molecular weight of 1800, and 125 parts of 4,4'-diphenylmethane diisocyanate were allowed to react with each other for 2 hours at 110° C. in a dry nitrogen atmosphere, and a prepolymer possessing an isocyanate group at the end was obtained. To this prepolymer, 937.5 parts of dry DMAC was added and dissolved, and stirred for about 1.5 hours at 20° C. While violently agitating the obtained solution, a chain extender solution obtained by dissolving well 13.8 parts of ethylene diamine and 0.5 part of diethylamine to 937.5 parts of dry DMAC, was added gradually. After heating the solution to 50° C., it was stirred for about 5 hours, and a viscous stock solution of viscosity of 400 poise at room temperature was obtained.

While stirring the stock solution, when a large amount of methanol was gradually added, the liquid became milky white, and a sediment of polymer was obtained. After filtering the sediment and washing it in a large amount of water, it was dried sufficiently. Furthermore, by Soxhlet extraction sufficiently in the sequence of acetone, ethanol and water, polyurethane urea was obtained. Its degree of swelling in water was 30% and moisture absorption rate was 140%.

To 15 parts of the obtained sediment of polyurethan urea, 45 parts of DMAC was added and dissolved well, which was used as a polymer mother liquor. As an antithrombotic, 1.5 parts of cilostazol was added to 15 parts of DMAC and dissolved sufficiently, and this mixture was added to the polymer mother liquor, and mixed violently. The obtained liquid was uniformly applied on the surface of a stainless steel bar of 3.0 mm in outside diameter, and immersed in 40° C. water bath for 30 minutes to be solidified. The obtained tube was drawn out of the stainless steel bar, washed in a large amount of water dried for 72 hours at 40° C., 0.1 mmHg, and DMAC and water were removed.

The obtained tube was, in dry state, 2.3 mm in inside diameter and 0.2 mm in wall thickness, and was suitable as an artificial blood vessel.

Example 6

To vary the degree of swelling and moisture absorption rate of the tubes in Example 1 and Example 3, polyol was changed. Specifically, as polyether diol, a block copolymer having ethylene oxide added to both ends of polyoxytetramethylene glycol and having a molecular weight of 2000 and about 10 mol % of a polyoxyethylene group was used as the polyether diol component, and the other preparation conditions were same as in Example 1, and polyurethane urea with moisture absorption rate of 1.7% was obtained (apparently, however, swelling could not be observed). To 20 parts of this polymer, 120 parts of DMAC was added and dissolved well, which was used as a polymer mother liquor. Next, as an antithrombotic, 2.0 parts of cilostazol was added to 24.6 parts of DMAC and dissolved sufficiently, and this mixture was added to the polymer mother liquor, and mixed violently. The obtained liquid was uniformly applied to the surface of stainless steel bar of 4.0 mm in outside diameter, and immersed for 60 minutes in 40° C. water bath, and solidified. The obtained tube was drawn out of the stainless steel bar, washed in a sufficient amount of water, and dried in air overnight, and dried in vacuo for 72 hours at 40° C., 0.1 mmHg to remove the residual DMAC and water were removed by force.

Figure 1D:
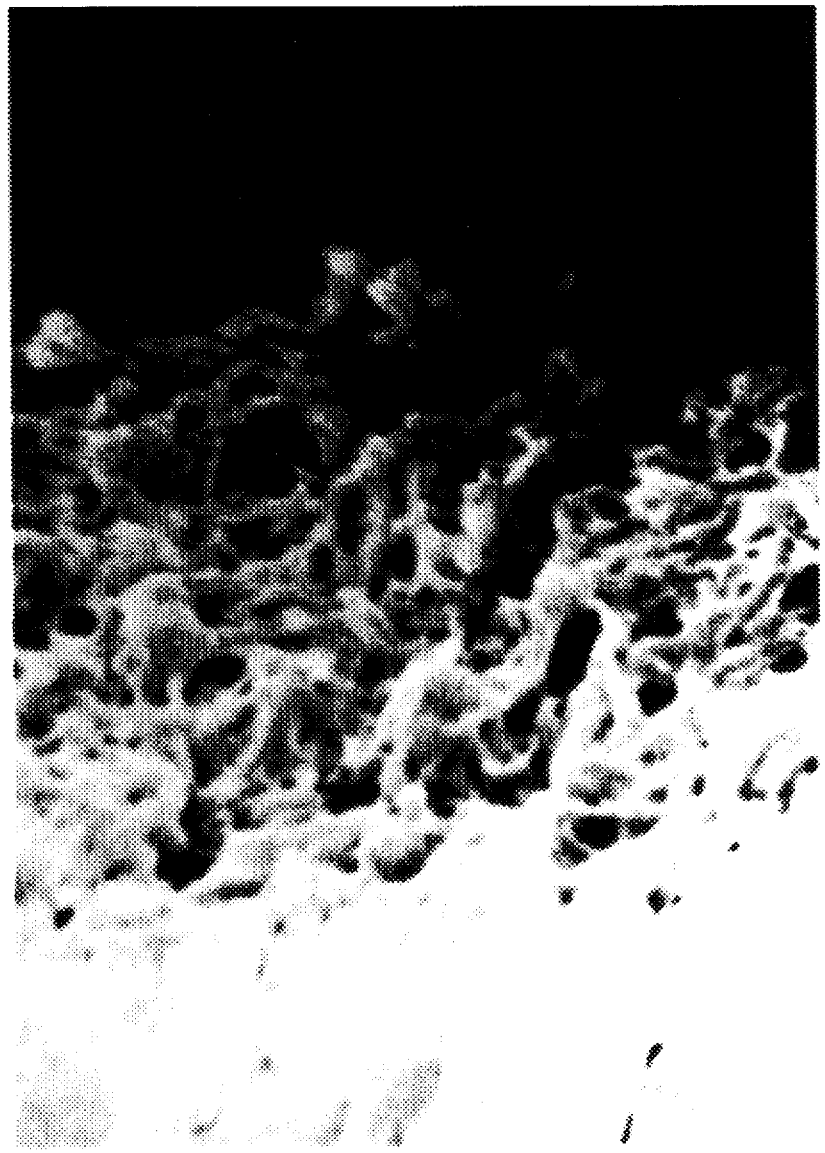

The obtained tube was, in dry state, 3.3 mm in inside diameter, 0.2 mm in wall thickness, and was suitable as an artificial blood vessel. This tube was porous as shown in the electron microscopic structure in FIGS. 1 (a) to (d), and was particularly favorable as an artificial blood vessel.

Example 7

A sediment of polyurethane urea was obtained in the same manner as in Example 3, except that a block copolymer having ethylene oxide added to both ends of polyoxypropylene glycol and having molecular weight of 2000 containing about 40 mol % of polyoxyethylene group was used as a polyether diol. In succession, using this polymer, a DMAC solution blending the polymer:cilostazol at a rate of 10:1.5 (by weight) was applied uniformly on the surface of a stainless steel bar of 3.0 mm in outside diameter, and immersed in 40° C. water bath for 30 minutes to be solidified. The obtained tube was drawn out of the stainless steel bar, washed in a sufficient amount of water, dried for 72 hours at 40° C., 0.1 mmHg, and the DMAC and water were removed.

The obtained tube was, in dry state, 2.6 mm in inside diameter, 0.2 mm in wall thickness, and was suitable as an artificial blood vessel.

Example 8

380 parts of polyoxytetramethylene glycol with a molecular weight of 1900, and 85 parts of 4,4'-diphenylmethane diisocyanate were allowed to react with each other for 2 hours at 70° C. in a dry nitrogen atmosphere, and a prepolymer possessing an isocyanate group at the end was obtained. To this prepolymer, 465 parts of dry DMAC was added and dissolved, and stirred for 3 hours at 10° C. In succession, while violently agitating the obtained solution, to 1216 parts of dry DMAC, a chain extender solution dissolving well 8.63 parts of ethylene diamine and 0.43 part of diethylamine was gradually added. The solution was heated to 40° C. and stirred for about 1 hour, and a viscous stock solution of viscosity of 500 poise was obtained. By adding 15 parts of acetic anhydride successively, the amino group terminal of the polymer was processed.

Next, while stirring the stock solution, when a large amount of methanol was gradually added, the liquid became milky white, and a sediment of polymer was obtained. After filtering the sediment and washing with a large amount of water, it was dried sufficiently. Furthermore, by sufficient Soxhlet extraction in the sequence of acetone, ethanol and water, polyurethane urea was obtained. Its degree of swelling in water was not observed apparently, and the moisture absorption rate was about 1.2%.

To 20 parts of thus obtained sediment of polyurethane urea, 124.7 parts of DMAC was added and dissolved well, and passed through a filter of 10 um, and the filtrate was used as a polymer mother liquor. Next, as an antithrombotic, 2 parts of cilostazol was added to 18 parts of DMAC and dissolved, and this mixture was added to the polymer mother liquor, and mixed violently. The obtained liquid was uniformly applied on the surface of a stainless steel bar of 3.0 mm in outside diameter, and immersed in 40° C. water bath for 1 hour to be solidified. The obtained tube was drawn out of the stainless steel bar, and washed with a sufficient amount of water, and dried for 72 hours at 50° C., 0.1 mmHg, so that the DMAC and water were removed.

The obtained tube was, in dry state, 2.7 mm in inside diameter, 0.2 mm in wall thickness, and was suitable as an artificial blood vessel.

Example 9

63.3 parts of polyethylene glycol with a molecular weight of 2000, and 29.5 parts of 4,4'-diphenylmethane diisocyanate were allowed to react with each other for 2 hours at 120° C. in a dry nitrogen atmosphere, and a prepolymer possessing an isocyanate group at the end was obtained. This prepolymer was moderately stirred and when cooled to 60° C., the rotating speed of the agitating blades of the reactor was raised to agitate violently, and 7.3 parts of 1,4-butane diol was charged at once. After continuing the blend for 7 minutes in this state, the reaction product was promptly taken out of the reactor, and put in a thermostatic oven controlled at 40° C. and relative humidity of 85% for 48 hours. Then, the finely pulverized reaction product was dried sufficiently, and charged into the extruder, and pellets were obtained from the extruder nozzle set at the temperature of 225° C. The obtained pellets were thermoplastic polyurethane that can be formed by extrusion, and the measured content of nitrogen in the polymer was 3.4% (calculated value: 3.3%). The degree of swelling of the polyurethane pellets in water and moisture absorption rate were measured in the method conforming to JIS K 7114, and the degree of swelling was 35% and the moisture absorption rate was 110%.

To 12 parts of the obtained pellet-form polyurethane, 24 parts of DMAC was added and dissolved well, which was used as a polymer mother liquor. Next, as an antithrombotic, 1.2 parts of cilostazol was added to 12 parts of DMAC and dissolved, and the mixture was added to the polymer mother liquor, and mixed violently. The obtained liquid was uniformly applied on the surface of a stainless steel bar of 3.0 mm in outside diameter, and immersed in 40° C. water bath for 30 minutes to be solidified. The obtained tube was drawn out of the stainless steel bar, washed with a sufficient amount of water, and dried for 60 hours at 40° C., 0.1 mmHg, so that the DMAC and water were removed.

The obtained tube was, in dry state, 2.3 mm in inside diameter, 0.2 mm in wall thickness, and was suitable as an artificial blood vessel.

Example 10

In a container containing 88 parts of DMAC, 9.6 parts of the polymer obtained in Example 6 and 2.4 parts of the polymer obtained in Example 1 were charged and agitated violently to prepare a polymer mother liquor. As an antithrombotic, 1.2 parts of cilostazol was added to the polymer mother liquor, and sufficiently agitated and dissolved. The obtained liquid was applied uniformly on the surface of a stainless steel bar of 4.0 mm in outside diameter, and immersed in 40° C. water bath for 40 minutes to be solidified. The obtained tube was drawn out of the stainless steel bar, washed in a sufficient amount of water, and dried for 72 hours at 40° C., 0.1 mmHg, so that the DMAC and water were removed. The obtained tube was, in dry state, 3.3 mm in inside diameter, 0.2 mm in wall thickness, and was suitable as an artificial blood vessel.

Test 1

In order to compare and study the duration of drug elution, the elution test was conducted in the following method, by using the antithrombotic tube manufactured in Example 1 (degree of swelling 26%, moisture absorption rate 120%), the antithrombotic tube manufactured in Example 4 (degree of swelling 30%, moisture absorption rate 90%), the antithrombotic tube manufactured in Example 6 (no apparent swelling, moisture absorption rate 1.7%), and the antithrombotic tube manufactured in Example 9 (degree of swelling 35%, moisture absorption rate 110%).

Measuring method

The tube was cut to a weight of about 200 mg, and put in a 100 ml stoppered Erlenmeyer flask containing 20 ml of elution solution (pH 7.4 physiological saline) preheated to 37° C., and shaken at 37° C. by using an incubator (manufactured by Taiyo Kagaku Kogyo, M-100) (at adjustment graduation 5). The tube was taken out in 30 minutes, and transferred into another 100 ml stoppered Erlenmeyer flask containing 20 ml of elution solution heated to 37° C., and shaken at 37° C.

Thereafter, the same. operation was repeated every 30 minutes. Each elution solution was filtered through a 0.45 um filter, and the filtrate was collected as sample solution.

Separately, 40 mg of cilostazol was weighed precisely, and acetonile was added to make up 200 ml to prepare a cilostazol standard stock solution (200 µg/ml). Precisely weighing 5 ml each of the cilostazol standard stock solution, 50% acetonitrile was added to make up 100 ml exactly as a standard solution (10 µg/ml).

Figure 2:
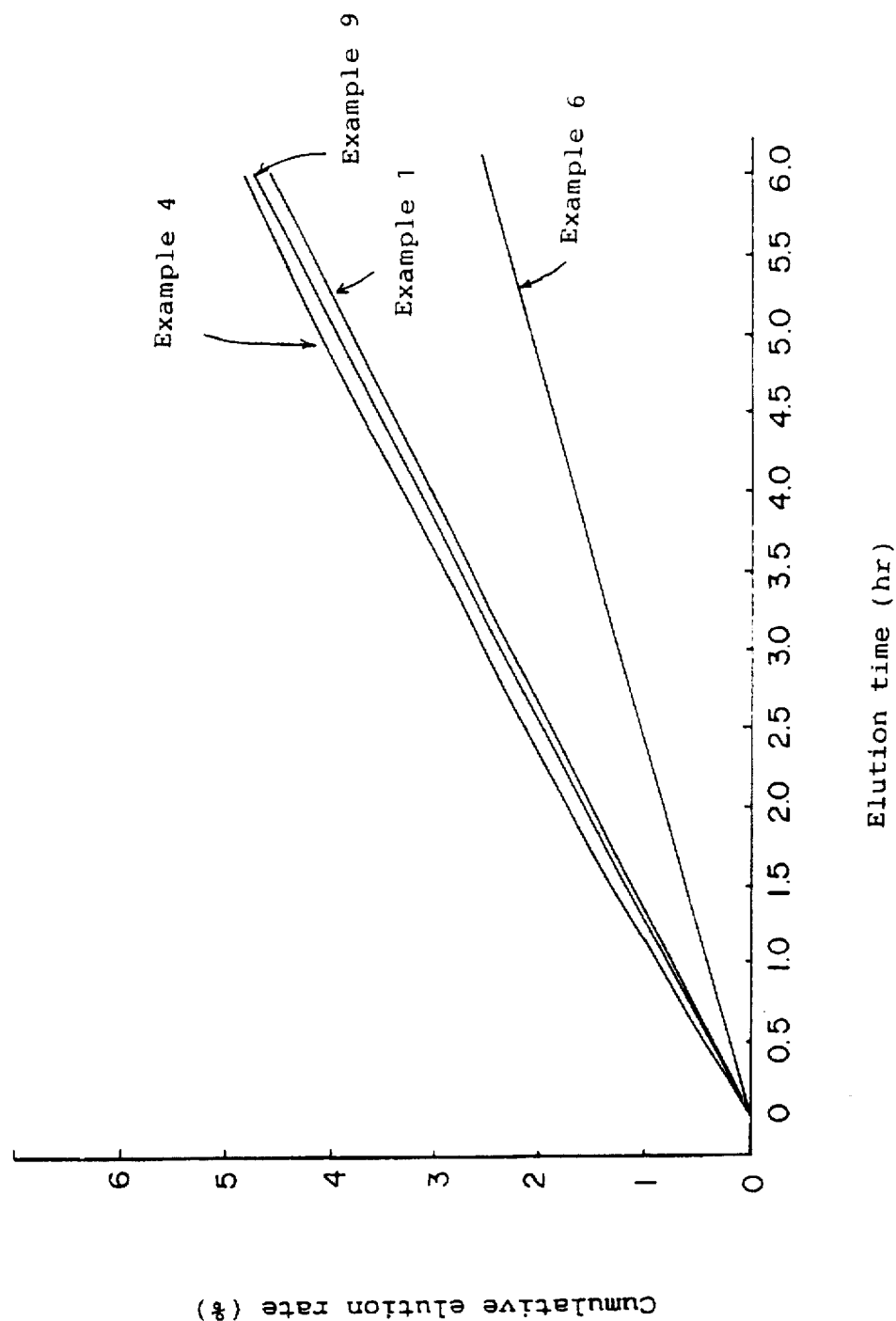
FIG. 2 is a graph showing the relation between the elution time and the drug cumulative elution rate, using the antithrombotic tubes obtained in Examples 1, 4, 6 and 9.

In the sample solution and standard solution, measuring by the following HPLC apparatus and in the following conditions, the cumulative elution rate was determined in the following formula. The test result is shown in FIG. 2.

HPLC apparatus

Pump: 510, Nippon Millipore Limited Waters

Detector: UVIDEC-100-V, Nippon Bunko Kogyo

Data processor: Data Module 741, Nippon Millipore Limited Waters

Auto sampler: AS-8000, Tosoh Corporation HPLC conditions

Column: Finepak SIL 18 T-5 (4.6 mm ID×250 mm)

Mobile phase: Acetonitrile, 10 mM phosphate buffer solution (pH 2.4) mixed solution (60:40)

Wavelength: 240 nm

Injection volume: 20 µl

Flow rate: 1.0 ml/min

Sensitivity: ATTENUATION 32

Column temperature: Room temperature $$\text{Cumulative elution rate (\%)} = \frac{M}{S \times P} \times 100$$

where M: cumulative elution amount (mg)

S: sample amount (mg)

P: drug (cilostazol) content (%)/100

The pH 7.4 physiological saline used herein was prepared by adding water to 1.3609 g of potassium dihydrogenphosphate to make up 50 ml exactly, adding 39.5 ml of 0.2N sodium hydroxide solution to produce a pH 7.4 buffer solution, and adding 25 ml of this solution to 500 ml of physiological saline.

Test result

As is clear from FIG. 2, cilostazol in the antithrombotic tubes of Examples 1, 4, 9 eluted at a concentration close to the solubility in the first 30 minutes, maintained the elution at nearly the same concentration for 6 hours. As it was estimated, such prolonged elution was maintained because cilostazol is taken into the molecular structure of polyurethane or polyurethane urea, and crystallization is blocked so that it is blended in the tube in a other state than needle crystals, for example, amorphous state.

Incidentally, in another experiment, when cilostazol was blended in the tube in a state of needle crystals, almost no elution was noted.

On the other hand, as is clear from the result of Example 6 shown in FIG. 2, by changing the type of polyetherdiol as the material for polymerization of polyurethane or polyurethane urea, it is also possible to adjust the elution rate so as to elute at a lower concentration than the solubility of cilostazol.

Therefore, the antithrombotic tubes of the invention are judged to be preferably used as medical materials such as artificial blood vessels.

Meanwhile, the cumulative elution rate in 5 hours of elution time was 3.8% in Example 1, 3.9% in Example 9, and 2.1% in Example 6, according to FIG. 2.

Test 2

A Japanese white rabbit was laparotomized under anesthesia by Nembutal, and the vena cava inferior was separated and exposed. After intravenous injection of 50 U/kg of heparin, the vena cava inferior was clamped immediately beneath the renal vein and immediately above the inferior mesenteric artery, and about 1 cm of the vena cava inferior was cut off. In succession, the antithrombotic artificial blood vessel of 2.9 mm in inside diameter obtained in Example 4 (degree of swelling 30%, moisture absorption rate 90%, 10% of cilostazol as antithrombotic), and an artificial blood vessel without cilostazol as a control (degree of swelling 30%, moisture absorption rate 90%) were cut to a length of 3 cm, and the wound was anastomosed end to end with 7–0 Spiren thread, and the abdomen was closed.

Figure 3A:
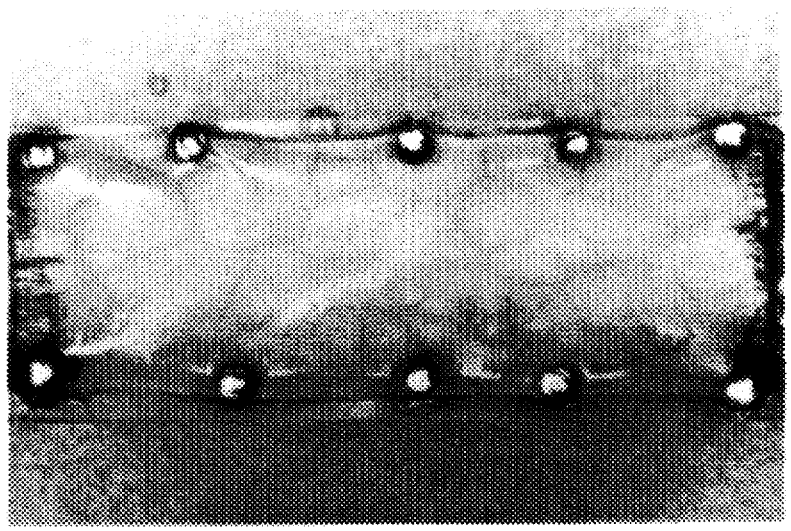
FIG. 3 (a) and (b) are photographs showing the test results of Test 2 conducted by using artificial blood vessel obtained in Example 4 and the control artificial blood vessel, respectively, FIG. 4 (a), (b) and (c) are photographs showing the test results conducted by the same manner as Test 2, except for using the artificial blood vessel of Example 6, and respectively show the states of the artificial blood vessel of 3 days, 7 days and 14 days after transplanting, and FIG. 4 (d), (e) and (f) are photographs showing the test results conducted by the same manner as Test 2, except for using the control artificial blood vessel, and respectively show the states of the artificial blood vessel of 3 days, 7 days and 14 days after transplanting.
Figure 3B:
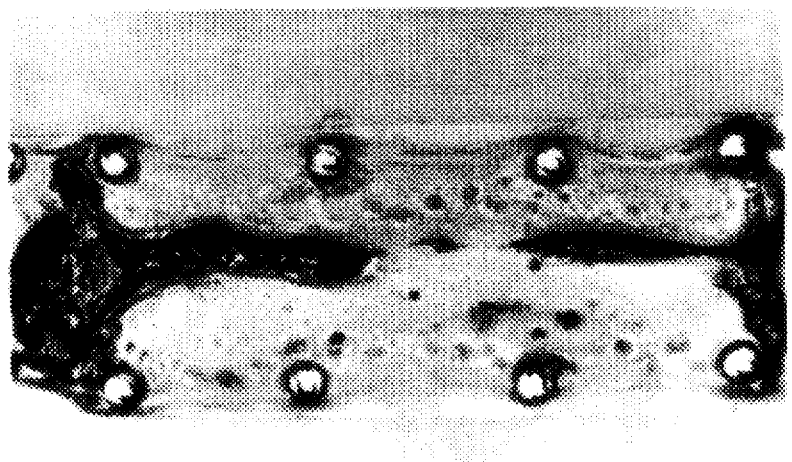
Figure 4A:
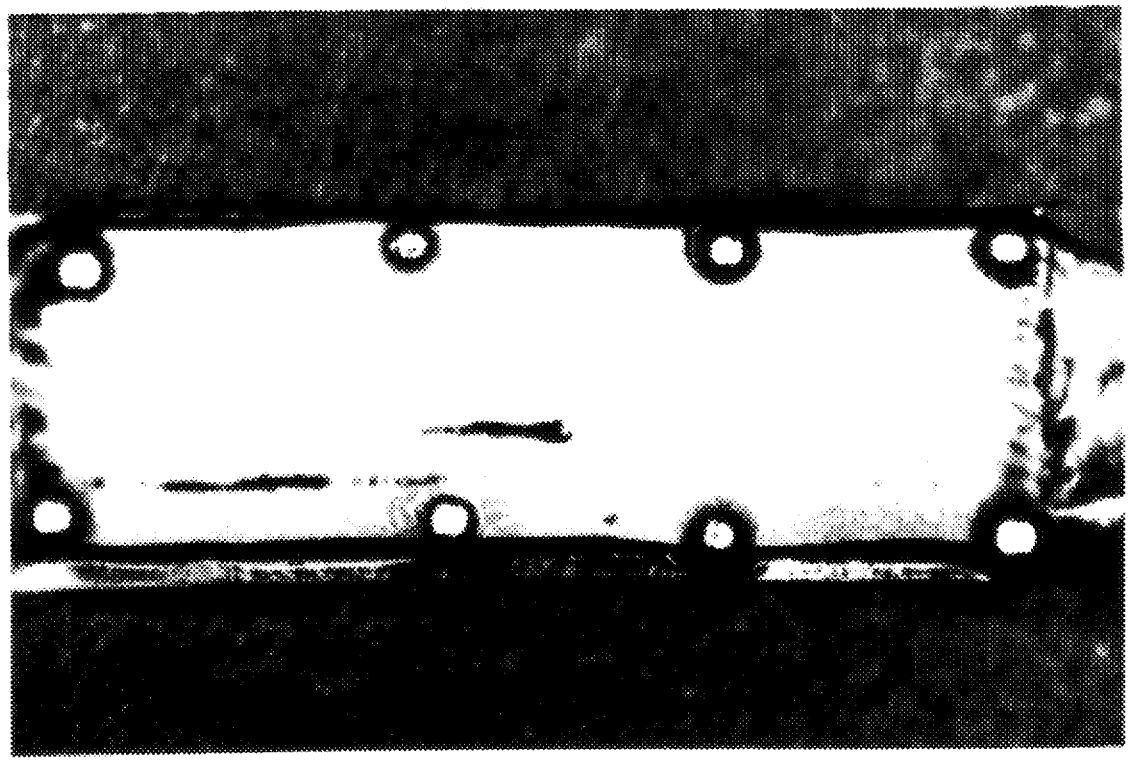
Figure 4B:
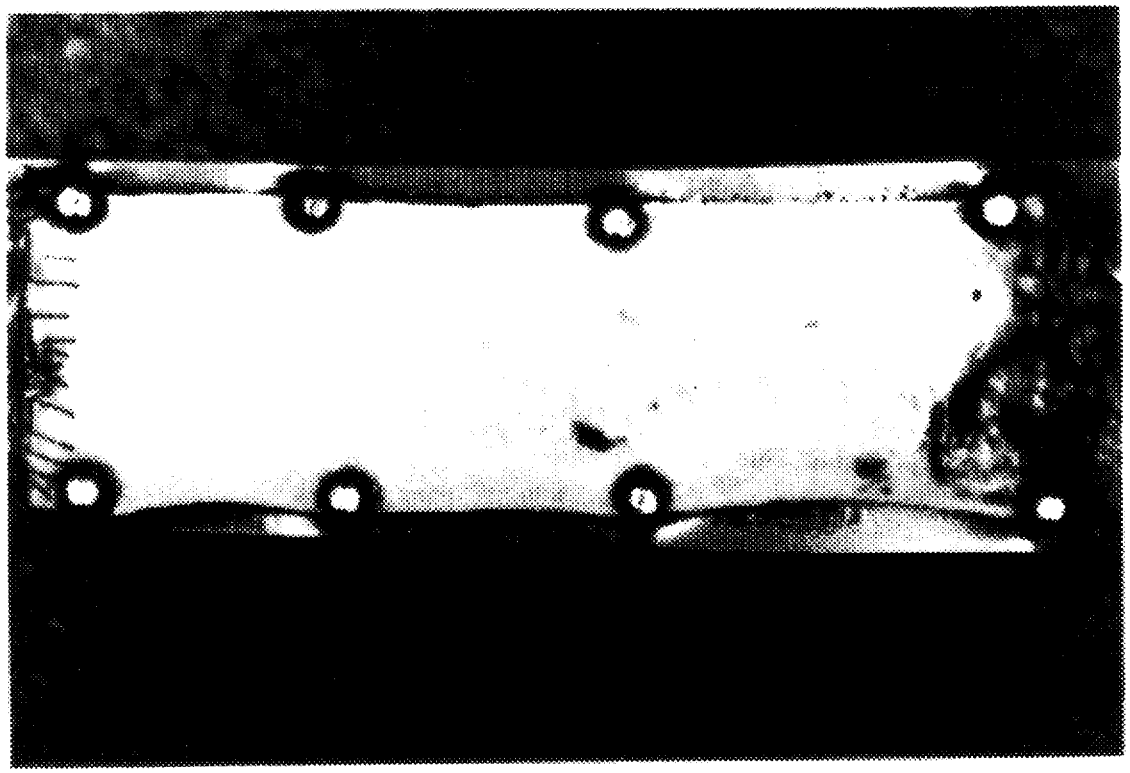
Figure 4C:
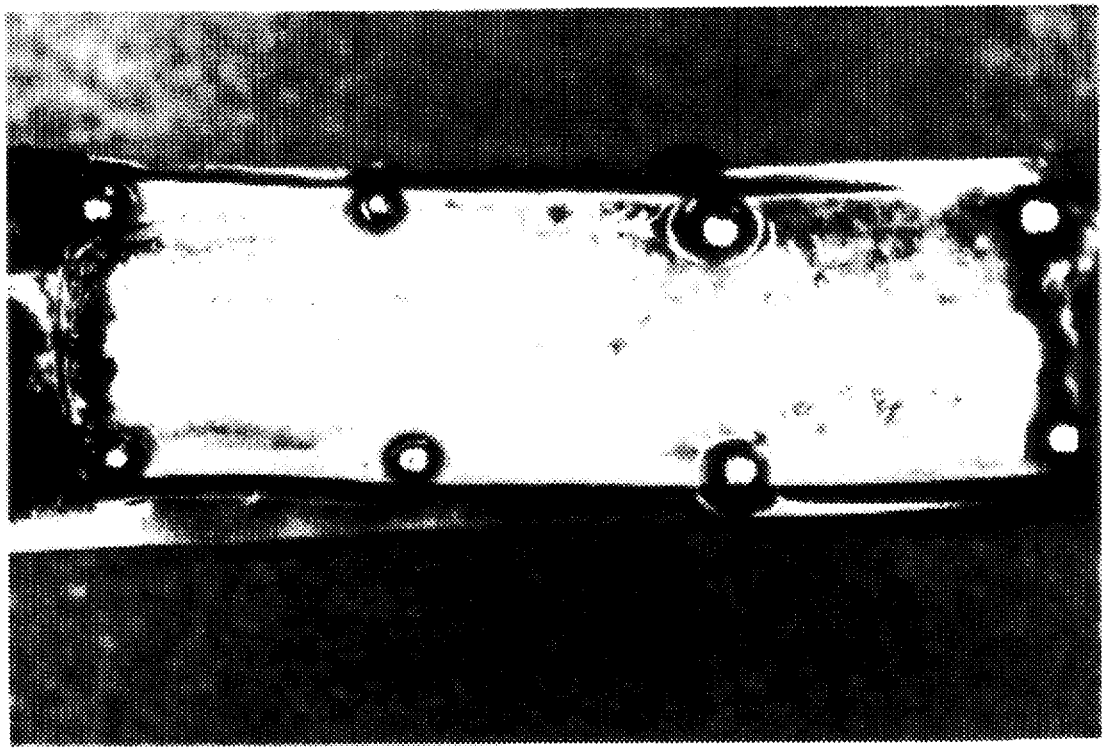
Figure 4D:
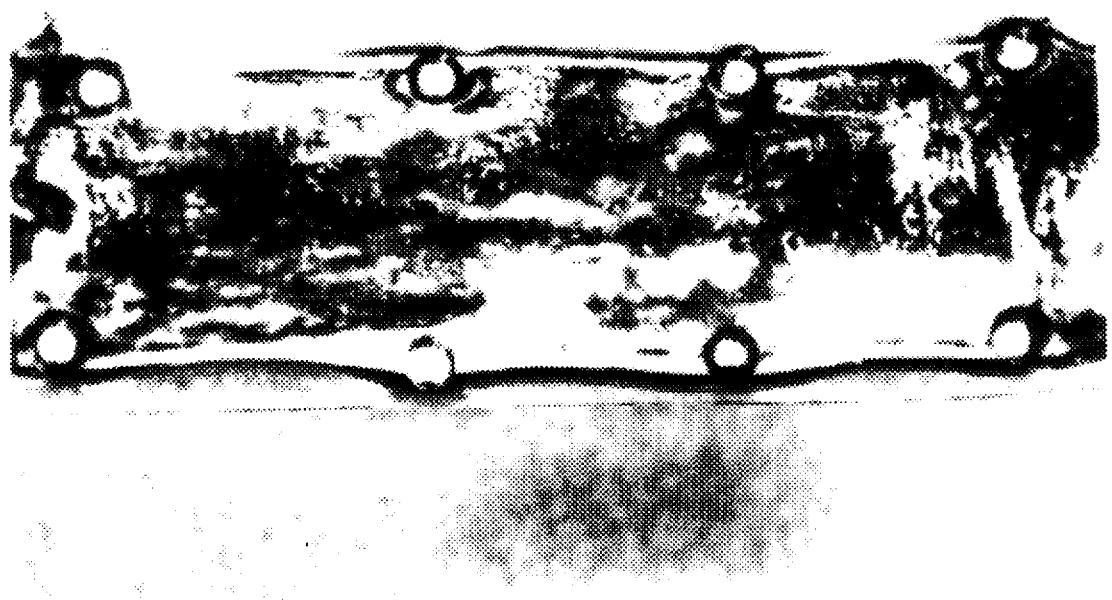
Figure 4E:
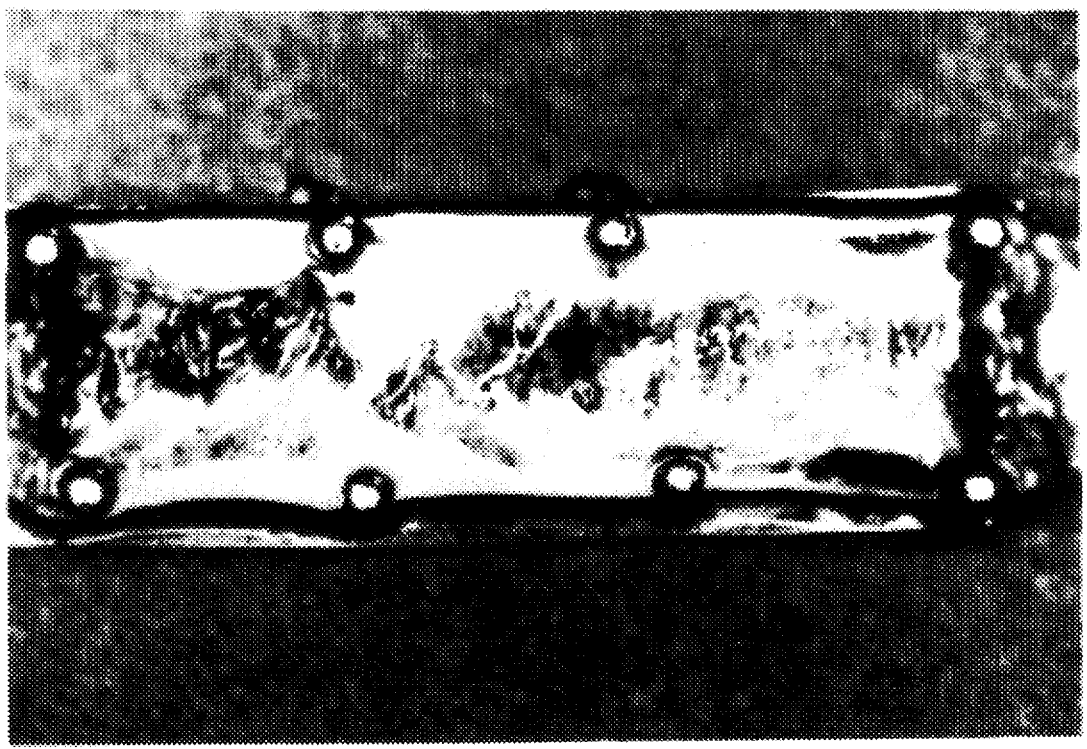
Figure 4F:
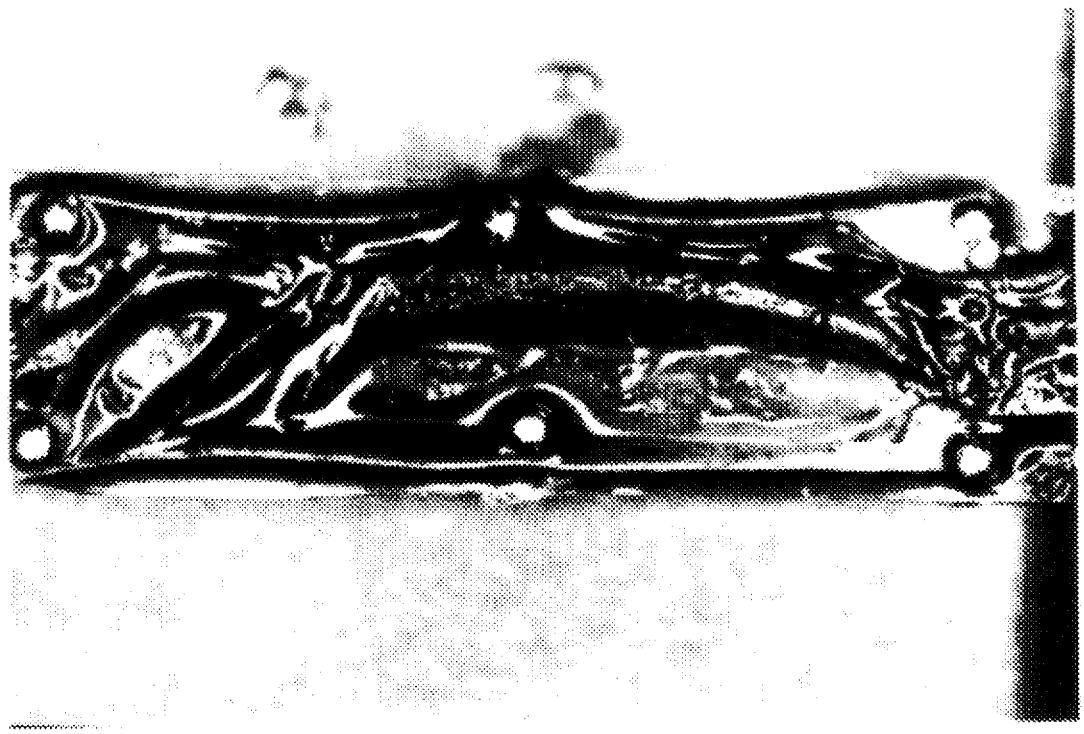

After a 24-hour observation, the animal was laparotomized again, 50 U/kg of heparin was intravenously injected, and the artificial blood vessel was taken out. The removed artificial blood vessel was immediately immersed in 2.5% glutaraldehyde solution, incised in the axial direction, and the inner space side was observed grossly and photographed (see FIGS. 3 (a) and (b)). In FIG. 3 (a), left is tail side, right is head side. Meanwhile, in FIG. 3 (b), right is tail side and left is head side. Blood is streamed from tail side to head side.

As a result, a thrombus was formed in the control artificial blood vessel shown in FIG. 3 (b), while no thrombus was formed at all in the antithrombotic artificial blood vessel obtained in Example 4 even after a relatively long time, as shown in FIG. 3 (a). Therefore, the antithrombotic artificial blood vessel of the invention is suggested to be extremely useful even when used as an artificial blood vessel of small aperture with the inside diameter of 4 mm or less.

On the other hand, FIGS. 4 (a), (b) and (c) show the test results conducted by the smae manner as in Test 2, except for using the artificial blood vessel obtained in Example 6. FIGS. 4 (a), (b) and (c) show the states in 3 days, 7 days and 14 days after transplanting, respectively. Also, FIGS. 4 (d), (e) and (f) are photographs showing the test results conducted by the same manner as in Test 2, except for using the control artificial blood vessel not containing cilostazol. FIGS. 4 (d), (e) and (f) show the states in 3 days, 7 days and 14 days after transplanting, respectively.

It is understood from each of the corresponding photographs (i.e. FIG. 4 (a) and FIG. 4 (d), FIG. 4 (b) and FIG. 4 (e), and FIG. 4 (c) and FIG. 4 (f)) that the antithrombotic artificial blood vessel of the invention can maintain the effect for a long time.

What is claim is:

1. An antithrombotic resin comprising a polyurethane or polyurethane urea resin having dispersed therein an antithrombotic agent in an amount of 0.1 to 50% by weight to the polyurethane or polyurethane urea resin, wherein said antithrombotic agent is cilostazol, and wherein said polyurethane or polyurethane urea resin has been prepared by polymerizing at least one polyether diol selected from the group consisting of a polyol containing a polyoxyethylene group expressed by formula (I):

  (I)

where n is a number-average degree of polymerization of 1 to 100, and a polyol containing a polyoxytetramethylene group expressed by formula (II):

  (II)

where m is a number-average degree of polymerization of 1 to 100.

2. An antithrombotic resin of claim 1, wherein the polyether diol comprises two or more polyols containing the polyoxyethylene group expressed by formula (I).

3. An antithrombotic resin of claim 1, wherein the polyether diol comprises at least one type of the polyol containing the polyoxyethylene group expressed by formula (I) and the polyol containing the polyoxytetramethylene expressed by formula (II).

4. An antithrombotic resin of claim 1, wherein the polyether diol is polyoxyethylene glycol.

5. An antithrombotic resin of claim 1, wherein the polyether diol is polyoxytetramethylene glycol.

6. An antithrombotic resin of claim 3, wherein the polyether didol comprises polyoxyethylene glycol and polyoxytetramethylene glycol.

7. An antithrombotic resin of claim 1, wherein the antithrombotic agent is present in an amount of 0.1 to 50% by weight of a mixture of two or more types of polyurethane or polyurethane urea resin.

8. An antithrombotic tube prepared by forming the antithrombotic resin of claim 1 in a tube form.

9. An antithrombotic film prepared by forming the antithrombotic resin of claim 1 in a film form.

10. An antithrombotic coating prepared by coating the surface of a medical apparatus with the antithrombotic resin of claim 1.

11. The antithrombotic tube according to claim 8, wherein the antithrombotic tube has a diameter of not more than 4 mm.

* * * * *